United States Patent [19]
Likuski

[11] Patent Number: 5,932,080
[45] Date of Patent: Aug. 3, 1999

[54] MOBILITY-BASED AND NORMALIZED CAPILLARY ELECTROPHORESIS

[75] Inventor: Robert K. Likuski, Castro Valley, Calif.

[73] Assignee: Bio-Rad Laboratories, Inc., Hercules, Calif.

[21] Appl. No.: 08/866,282

[22] Filed: May 30, 1997

[51] Int. Cl.⁶ .................................................. G01N 27/26
[52] U.S. Cl. ........................................ 204/451; 204/452
[58] Field of Search ..................................... 204/451–455

[56] References Cited

U.S. PATENT DOCUMENTS

| | | |
|---|---|---|
| 3,941,678 | 3/1976 | Akiyama . |
| 4,920,498 | 4/1990 | Kaneko . |
| 5,139,630 | 8/1992 | Chen . |
| 5,316,630 | 5/1994 | Dasgupta . |

FOREIGN PATENT DOCUMENTS

| | | |
|---|---|---|
| 0 517 370 A1 | 12/1991 | European Pat. Off. . |
| WO96/34946 | 11/1996 | WIPO . |

OTHER PUBLICATIONS

J.L. Beckers et al. *Journal of Chromatography* (1988) 452: 591–600.

Ju Yang et al., "Improved Reproducibility in Capillary Electrophoresis Through the Use of Mobility and Migration Time Ratios," *Journal of Chromatography A* (1996) 735: 209–220.

J.L. Beckers et al., "Determination of Absolute Mobilities, pK Values and Separation Numbers by Capillary Zone Electrophoresis, Effective Mobility as a Parameter for Screening," *Journal of Chromatography* (1991) 537: 407–428.

*Primary Examiner*—William H. Beisner
*Attorney, Agent, or Firm*—Townsend and Townsend and Crew LLP

[57] ABSTRACT

Identification and quantification of constituents of a sample is achieved by mobility-based electropherograms obtained from capillary electrophoresis, the mobilities being normalized by zero correction followed by division by the mobility of a selected marker. Zero correction is achieved either relative to a separate marker or by calculation based on the same marker. The resulting electropherograms are more recognizable since they more closely resemble the scanned separation patterns obtained with planar gels, and individual constituents of the sample are more easily and reliably identified since their positions in the electropherogram are substantially constant from one electropherogram to the next and hence reproducible to a high degree of accuracy.

33 Claims, 5 Drawing Sheets

MOBILITY-BASED AND NORMALIZED CAPILLARY ELECTROPHORESIS

BACKGROUND OF THE INVENTION

Capillary electrophoresis has developed into a highly effective means of analyzing biological samples. Capillary electrophoresis encompasses a large variety of separation modes, many of which provide separations that equal or exceed the quality of separations that can be performed on slab gels. One form of capillary electrophoresis that is particularly suitable and convenient for many separations is capillary zone electrophoresis (CZE). Other forms include capillary isoelectric focusing, capillary gel electrophoresis, capillary isotachophoresis, micellar electrokinetic chromatography, and capillary electroosmotic chromatography. Capillary electrophoresis further offers an easy interface to digital computers and the consequent opportunities for automated control and sophisticated data handling, processing and display. The long separation path in a capillary permits the separation of a large number of components in a single sample, including components which are closely related. Also, separations can be performed in relatively short periods of time by using high voltages, since the small diameter and thin wall of a capillary provide efficient removal of the joule heat generated by the voltage. Capillaries are also well suited for on-line detection of the separated species by passing a light beam either through the capillary and directly into a detector or into the capillary to activate a fluorescently labelled species.

When the inner wall of the capillary carries a fixed electrical charge, electroosmosis occurs. Electroosmosis is a bulk flow of the solvent in which the analytes migrate. Electroosmosis is particularly pronounced in capillaries made of silica-containing materials, unless special efforts are made to coat the inner wall of the capillary or otherwise shield the charge on the inner wall. In untreated silica capillaries, the charge on the wall is negative, resulting in a bulk flow from the positive anode to the negative cathode. Because of this bulk flow, both positively and negatively charged analytes can be loaded at the anode and detected near the cathode. Although negatively charged analytes tend to migrate toward the anode, they are carried toward the cathode by the bulk flow if the magnitude of the velocity of the bulk flow exceeds that of the negative analyte.

Positively charged analytes, however, are not well suited to separations in capillaries with negatively charged inner walls since the particles tend to adhere to the walls. Were it not for this problem, the electroosmotic flow would increase the apparent rate at which positively charged analytes migrate from anode to cathode. Negatively charged analytes by contrast are repelled from the negatively charged inner wall, thereby significantly reducing the adherence of analytes to the wall.

The time taken for an analyte to reach the detector window is a non-linear function of both the electroosmotic and electrophoretic components of the velocity of the analyte. The sum of these two components appears in the denominator of the equation for the migration time. As the sum approaches zero, therefore (i.e., when the components become equal in magnitude but opposite in direction), the migration time increase toward infinity. When the electrophoretic component exceeds the electroosmotic component in magnitude, the analyte does not move through the capillary toward the cathode but instead returns to the inlet vial at the anode end of the capillary.

Variability in the magnitude of electroosmotic component limits the use of migration time as a means of identifying analytes. To eliminate the variability, electrophoretic velocity can be used instead of migration time. The electrophoretic or "actual" velocity is the difference between the total or "apparent" velocity and the electroosmotic velocity. (The term "velocity" is used herein to denote a directional value, i.e., one bearing a positive sign to denote one direction or negative sign to denote the opposite direction.) Under non-varying conditions, the electrophoretic velocity is an appropriate quantity for identifying analytes in a sample. When conditions vary, the variations can often be eliminated by using the ratio of the electrophoretic velocity of the analyte to the electrophoretic velocity of a standard compound run under the same conditions, preferably as part of the same sample. This ratio is referred to as a normalized velocity. An alternative to velocity is mobility, which is the ratio of velocity to field strength, and capable of normalization in the same manner as the velocity. The normalized velocity of a given analyte is equal to its normalized mobility.

Patient samples are analyzed by capillary electrophoresis in clinical laboratories either to screen for suspected conditions or to monitor the state of a known condition. For screening, the results are compared with established clinical standards, and for monitoring they may also be compared with previous results from the same patient. For this comparison, numerical values produced by mathematical manipulation of the data or visual displays produced from the data may be used. While the generation of accurate numerical values and appropriate visual displays share similar needs, the visual display model serves better to illustrate the need to express the information appropriately. In a particularly useful visual display referred to as an overlay, the electropherogram produced from a patient sample is superimposed either over a reference electropherogram or over an electropherogram generated from a sample collected at a different time from the same patient. For this overlay, it is important that the x-axis represent a quantity that is easily associated with the identity of a particular analyte and that the y-axis represent a quantity that is easily associated with the amount to the analyte present. The preferred method uses normalization of both axes and particularly normalized mobility for the x-axis.

A typical example of a method for normalization of migration time combined with zero correction is described in Chen, U.S. Pat. No. 5,139,630 (Beckman Instruments, Inc., issued Aug. 18, 1992). According to the Chen procedure, two marker species are added to the sample prior to separation. One of the marker species is uncharged and therefore has no electrophoretic mobility of its own, its travel being due solely to the bulk movement of the running buffer (i.e., the electroosmotic flow). The other marker species is charged with a charge density greater than that of the original components of the sample and thereby travels at a rate representing the sum of its electrophoretic velocity and the electroosmotic flow velocity. The detection peaks corresponding to the two markers thus bracket the peaks of the sample components, and the time axes of peak patterns for different samples are zeroed to the peak of the uncharged marker and normalized to the peak of the charged marker. These two peaks therefore occur at the same time in each electropherogram and the locations of all other peaks (and hence the identities of the solutes represented by the other peaks) are determined relative to these two.

One of the difficulties with peak normalization based on migration time is that it does not correct an inherent problem that arises when comparing capillary electrophoresis to electrophoresis performed in planar (slab) gels. In planar gels, the separation between components of the sample mixture is measured by terminating the electric current while the components are spread out along the gel, and detection and identification of the components is then performed by scanning the gel and recording the positions of the components on the gel (i.e., the migration distance of each component from the edge where the sample is first applied). In capillary electrophoresis, the electric current is maintained until all components have passed through the detection window, and detection and identification are therefore based on migration time rather than migration distance. With certain types of samples, this creates a noticeable difference in the appearance of the electropherogram. In serum protein separations, for instance, the gamma region in a capillary separation looks considerably different from the gamma region produced by a planar gel separation. The lack of familiar shapes makes capillary electrophoresis less appealing.

Another difficulty with the use of migration time as the x-axis arises from the fact that migration time depends strongly on the surface charge density on the inner wall of the capillary and that charge density can vary considerably from capillary to capillary, from run to run using the same capillary, and from sample to sample within the same run. Electrophoretic mobility, by contrast, does not depend on the surface charge density of the capillary wall. Although migration time normalization reduces the consequences of this dependency significantly, it does not eliminate the consequences entirely.

Difficulties arise with the use of a neutral marker for zero correction. The addition of an uncharged species to the sample to serve as a neutral marker often interferes with the separation pattern sought to be detected by producing a peak that overlaps or otherwise obscures or distorts sample component peaks occurring close by, such as the gamma region in a five-band serum protein separation. Native artifacts of the electropherogram such as a small peak near the beginning of the electropherogram can be used instead of an added uncharged species. These artifacts may also interfere with the pattern, and special adjustments such as increasing the detection wavelength are often done to eliminate them.

SUMMARY OF THE INVENTION

It has now been discovered that separation patterns obtained from capillary electrophoresis using zero corrected and normalized mobility as the horizontal axis present an unexpected improvement over separation patterns that use zero corrected and normalized migration time. The use of electrophoretic mobility rather than migration time as both the horizontal axis for the electropherogram and a normalization factor results in separation patterns that are closer in appearance to those produced by scanning planar gels, and produces separation patterns in which small differences are easier to detect when two or more patterns are superimposed for comparison. The effects of changing electroosmotic flow rates and environmental factors such as temperature, pH, voltage and capillary length, are all reduced. The separation patterns thus developed are useful in detecting the presence of and/or quantifying a single constituent species in a sample, or two or more constituent species in a single sample, or the entire sample composition.

Normalization can be performed relative to any selected marker in the running buffer, whether it be part of the sample itself or a component added to the buffer to co-dissolve with the sample components. The normalization marker can be one represented by a peak anywhere in the separation pattern that is at least substantially removed from the zero point. Thus, markers eluting either before, among, or after the peaks representing the sample components of interest can be used, although markers that elute after all components of interest (i.e., markers with mobilities having an absolute value exceeding the mobilities of all suspected constituent species in the sample) are preferred. Zeroing can likewise be performed relative to any selected marker in the running buffer (not necessarily a neutral marker). The marker can be an artifact (an identifiably distinct point in the shape of the electropherogram, such as a peak, a valley, or a sharp corner or directional change) that is characteristic of the sample or of the running buffer, or a component added to the buffer to co-dissolve with the sample components.

It has also been discovered that both normalization and zero correction can be achieved by use of a single charged marker and an estimated electrophoretic mobility for that marker without reference to either a neutral marker or an artifact of the electropherogram. Such zero correction is obtained from the migration time of the charged marker used for normalization along with an estimated value for the electrophoretic mobility of that marker. In certain embodiments of the invention, the mobility is estimated by including one or more reference samples in the run. The reference sample(s) will include the same charged markers and clearly discernable features in the detection peaks that are highly reproducible from one reference sample to the next. The expected location of these features along the x-axis is used instead of the location of a peak produced by an added neutral marker or an artifact in the electropherogram (such as a characteristic perturbation in the baseline). The use of normalized mobility as the x-axis makes the location of these features particularly stable.

Curve fitting methods can be used to take advantage of the information provided by several features in the electropherogram, the contribution of each feature being weighted according to the predetermined stability of its location from one sample to the next. One particularly convenient implementation consists of calculating the normalized mobilities of selected features from their migration times using estimated values for the electroosmotic mobility and the electrophoretic mobility of the marker. This set of normalized mobilities is referred to herein as a "feature set." A second set of corresponding normalized mobilities, referred to herein as a "master feature set," consists of expected values of the normalized mobilities for the same features that are determined statistically by running samples from the same reference lot with two, rather than just one, appropriate markers. Realizing that the crest of the marker peak is particularly stable and forcing the straight line fit through the normalized location of the markers in both the feature set and master set further improves the linear fit. The parameters defining the fitted straight line are then used to refine the estimate of the electrophoretic mobility of the reference sample marker.

As an alternative to feature fit, a pattern fit may be used. In a pattern fit, a master electropherogram is used instead of a master feature set and a value of the electrophoretic mobility of the reference sample is systematically determined such that the best correlation is achieved over selected sections of the reference electropherogram and the master electropherogram. Again, the markers in both the reference electropherogram and the master electropherogram are forced to have equal values of normalized mobility. The gamma region in a serum protein electropherogram is an appropriate region to use for the correlation. The electrophoretic mobility of the reference sample that gives the best correlation can be systematically determined by appropriate software. One example is the constrained non-linear minimization routine named "constr.m" from the MATLAB® Optimization Toolbox (Math Works, Inc., Natick Mass., USA).

These and other features, benefits and advantages of the invention are explained in further detail below.

DETAILED DESCRIPTION OF THE INTENTION AND PREFERRED EMBODIMENTS

Figure 1:
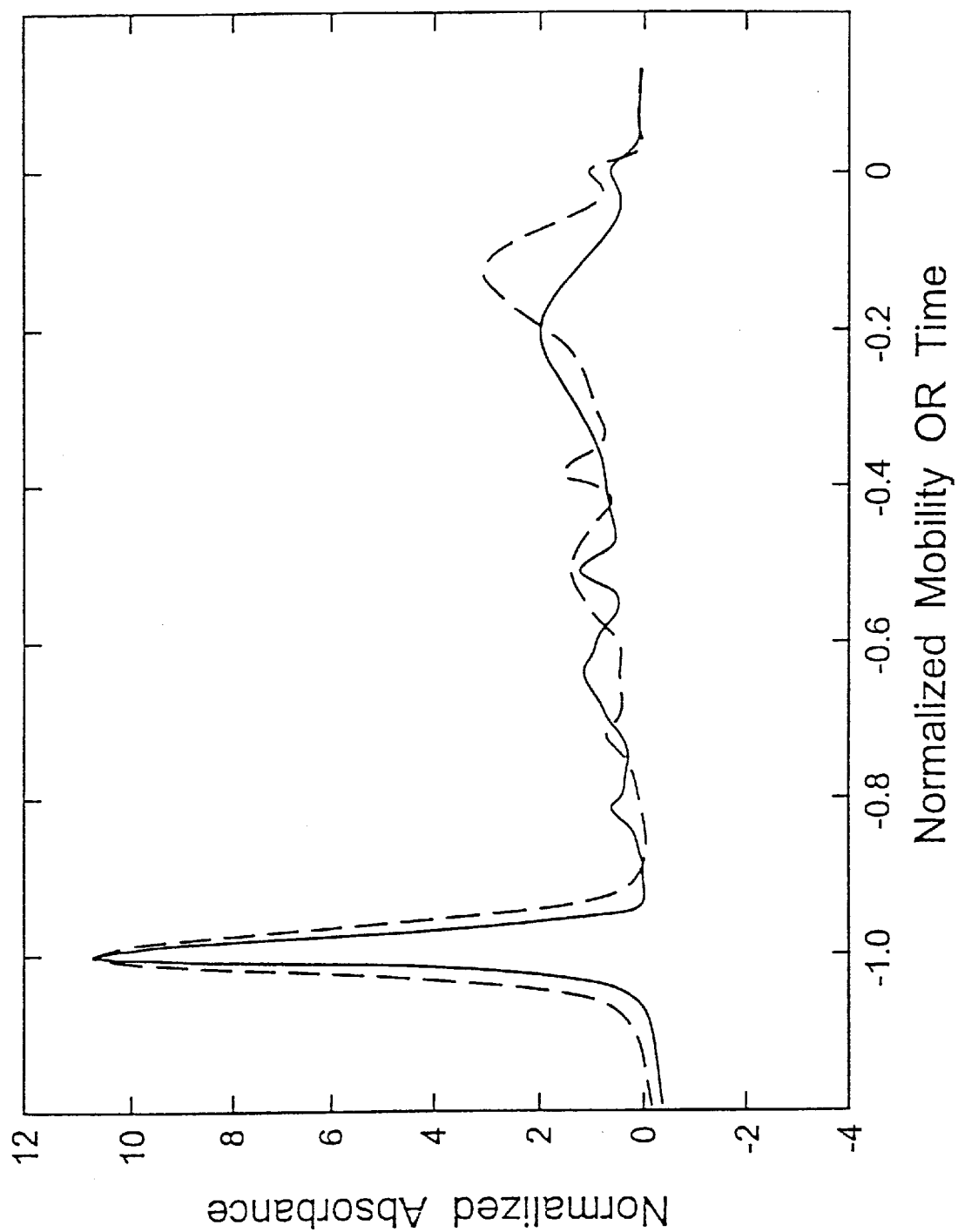
FIG. 1 is a superimposed plot of two electropherograms representing the same separation of a human serum sample. One electropherogram uses normalized time for the horizontal axis and the other uses normalized mobility, normalization in each case being relative to one of the constituents of the sample. The peaks are zero corrected relative to a peak that is an artifact of the electropherogram.

The total mobility $\mu$, as known in the art and also referred to as "apparent mobility," is defined as the ratio of the velocity v of a component in the longitudinal direction of the capillary (determined from the migration time t required to traverse the distance $L_d$ between the injection point and the detection window) to the electric field strength E, where E (for constant conductivity between input and output) is the applied voltage V divided by the total length $L_t$ of the capillary. Thus, The velocity $v_x$ of component x is related to its migration time $t_x$ by (1)

$$E = \frac{V}{L_t} \quad (2)$$

$$v_x = \frac{L_d}{t_x}$$

Therefore, $$\mu_x = \frac{v_x}{E} = \frac{L_d L_t}{t_x V} \quad (3)$$

Electroosmotic mobility $\mu_0$, or the mobility of a neutral species due to electroosmotic flow, is:

$$\mu_0 = \frac{L_d L_t}{t_0 V} \quad (4)$$

where $t_0$ is the migration time required for the neutral species to traverse the distance $L_d$. Thus, for component x, the zero-corrected mobility $\mu_{x0}$, is its total mobility $\mu_x$ minus the electroosmotic mobility $\mu_0$:

$$\mu_{x0} = \mu_x - \mu_0 = \frac{L_d L_t}{V}\left(\frac{1}{t_x} - \frac{1}{t_0}\right) \quad (5)$$

This zero-corrected mobility is also referred to as "electrophoretic mobility" or "actual mobility."

These relationships show that when a charged marker with a known electrophoretic mobility $\mu_{M0}$ (such as for example by independent determination in the same capillary) is used, the electroosmotic mobility $\mu_0$ can be determined without the use of either a neutral marker or an artifact of the separation pattern, by using the electrophoretic mobility $\mu_{M0}$ and the migration time $t_M$ of the charged marker according to the relationship:

$$\mu_{M0} = \mu_M - \mu_0 = \frac{L_d L_t}{V}\left(\frac{1}{t_M} - \frac{1}{t_0}\right) \quad (6)$$

Rearranging terms, $$\mu_0 = \mu_M - \mu_{M0} = \frac{L_d L_t}{V t_M} - \mu_{M0} \quad (7)$$

A normalized mobility is determined by dividing the electrophoretic mobility in Equation (5) by the electrophoretic mobility of the marker:

$$\mu_{nx} = \frac{\mu_{x0}}{\mu_{M0}} \quad (8)$$

Equations (4), (5), (7) and (8) indicate that either $t_x$ and $t_0$, or $t_x$ and $\mu_{M0}$ can be used to determine $\mu_{x0}$ and $\mu_{nx}$. A neutral marker or artifact is typically needed to deremine $t_0$. If neither is available, then a determination of $\mu_{M0}$ is needed. A reference sample, which can be included as the first sample in a set of patient samples, provides the means of making this determination of $\mu_{M0}$.

The determination of mobility $\mu_{M0}$ for a reference sample that has neither a neutral marker nor an artifact is referred to herein as a "feature fit." To achieve a feature fit, selected features of the reference sample are used in place of a neutral marker or artifact. The features that are selected or weighted most heavily are those that have the highest reproducibility. The first step in the feature fit method is to run the reference sample as a patient sample, using the best available estimate for the electrophoretic mobility of the marker, and designating a group of features of the electropherogram, typically selected crests and valleys. The normalized mobility of each feature in the group is compiled as a "feature set." A "master feature set" has been previously compiled by running with two, instead of one, markers a statistically significant set of samples from the same lot or from similar lots and determining the average of the normalized mobilities.

Once the feature set is obtained, it is used to refine the estimate of the electrophoretic mobility of the marker in the reference sample as follows:

1. Using the normalized mobilities of the selected master features as the x-axis of a scatter plot and the corresponding normalized mobilities from the feature set as the y-axis, a forced least mean squares straight line fit is made for the points representing the selected features. The straight line is forced through the coordinates of the point corresponding to the normalized mobilities of the marker for the master feature set and feature set (using −1, −1 as the coordinates, for example).

2. The y-value of the intercept of the fitted straight line and the y-axis at x=0 is then determined and assigned the symbol d (including its sign).

3. Using the value of d, a corrected value $\mu_{M0r}$ (the added subscript r signifying that this is the mobility of a reference) is determined, according to the formula $$\mu_{M0r} = \mu_{M0}(1+d) \qquad (9)$$

4. The corrected value of $\mu_0$ can be determined by the formula $$\mu_{0r} = \mu_0 - \mu_{M0}d \qquad (10)$$

5. The corrected value of any normalized mobility $\mu_{nr}$, (the added subscript n signifying that the mobility is normalized) in the reference can be determined by the formula $$\mu_{nr} = \frac{\mu_n - d}{1 + d} \qquad (11)$$

The value of $\mu_{M0r}$ determined in Step 3 is the electrophoretic mobility of the reference used to analyze all of the patient samples associated with the reference.

When the normalization marker is a charged species not present in the sample but added to it prior to the separation, the species is preferably one that is compatible (fully miscible) with the sample and inert relative to the sample constituents, will not affect their mobilities to anything more than a negligible degree, and are stable and non-volatile. The marker must also have a mobility that is as insensitive to the surrounding environment as possible. In particular, the charge on the marker should be relatively insensitive to small changes in pH and the effective size of the marker should not change due to structural changes or combination with other molecules. The preferred species will also form a sharp, well-defined peak after the last peak formed by the sample constituents, and not overlapping with the last sample constituent peak or any of the peaks of the sample. To achieve this in separations in which the direction of electrophoretic migration is opposite that of electroosmotic flow (in protein separations, for example), the preferred normalization marker will be a negatively charged species having a low molecular weight relative to the sample constituents so that its zero-corrected mobility has an absolute value greater than the constituents. In most applications, best results will be achieved with a normalization marker having a molecular weight of less than about 750, and preferably less than about 500, and most preferably less than about 250. A preferred range for the molecular weight is about 50 to about 750, more preferably about 75 to about 500, and most preferably about 100 to about 250. The electrophoretic character of the species can also be expressed in terms of its charge density, defined as the ratio of the number of negative charges on a molecule of the species (i.e., electron equivalents) to the molecular weight of the species. Best results will generally be achieved with species having a charge density of about 0.001 or greater, and preferably about 0.003 or greater. A preferred range for the charge density is about 0.001 to about 0.03, most preferably from about 0.003 to about 0.01.

For those embodiments of the invention in which detection is performed by direct absorbance, the most suitable charged species will also be one that has an absorbance within a wavelength range used by conventional and readily available detectors for capillary electrophoresis. The absorbance maximum is preferably about 300 nm or less, more preferably about 250 nm or less. In terms of ranges, the preferred range is about 180 nm to about 300 nm, and the most preferred is from about 200 nm to about 250 nm.

Examples of charged species suitable as added normalization markers for protein separations are hippuric (benzoylaminoacetic) acid, acetic acid, benzophosphoric acid, propionic acid, isopropionic acid, butyric acid, isobutyric acid, benzoic acid, benzosulfonic acid, o-chlorobenzoic acid, m-chlorobenzoic acid, p-chlorobenzoic acid, naphthylsulfonic acid, benzonaphthalinic acid, chlorobenzonaphthalinic acid, and chloronaphthyl sulfonic acid. Other examples will be readily apparent to those skilled in the art.

When a constituent already present in the sample is selected as the normalization marker, the constituent is preferably one whose presence is known to exist in each sample of the type represented by the sample to be analyzed, and most preferably one whose amount in each sample is known as well. The constituent will most likely be one that is not of concern, i.e., one whose quantity relative to the other constituents is not indicative of an abnormal condition or is not being monitored, and preferably one whose quantity is nonvariable or nearly so. As in the case of the added marker, the marker already present is preferably one that forms the last peak on the electropherogram, distinct from and non-overlapping with any of the other peaks, i.e., one with the largest electrophoretic mobility.

Zero correction can be achieved by a charged species (different from that used as the normalization marker) already present in the sample or added to the sample, by a neutral species already present in the sample or added to the sample, by an artifact of the electropherogram (i.e., a small peak or other identifiable contour feature of the electropherogram that is not representative of a constituent species), or by calculation based on parameters of the normalization marker.

When zero correction is achieved by the addition of an external species as the zero marker, species with extremely low charge density (lower than each of the sample constituents) or neutral species are preferred. Neutral species are the most preferred. Appropriate zero correction species will be those that, like the normalization marker species, are compatible (fully miscible) with the sample and inert relative to the sample constituents, will not affect the charge or mobility of the sample constituents to anything more than a negligible degree, and are stable and non-volatile. The preferred species will also form a sharp, well-defined peak before the first peak formed by the sample constituents, and not overlapping with the first constituent peak or with any other peaks in the electropherogram. In embodiments utilizing absorbance as the detection parameter, preferred neutral species, like the charged species, will have an absorbance within a wavelength range used by conventional and readily available absorbance detectors for capillary electrophoresis. The absorbance maximum for the neutral species is preferably about 300 nm or less, more preferably about 250 nm or less. In terms of ranges, the preferred range is about 180 nm to about 300 nm, and the most preferred is from about 200 nm to about 250 nm.

Examples of neutral species suitable to be added are mesityl oxide, methyl benzoate, isopropanol, methanol, ethanol, ethylene glycol, dimethyl formamide, formamide, neutral charge amino acids (i.e., with the amino group protected), and neutral charge peptides such as the N-acetyl methyl ester of glycine.

When zero correction is achieved by the use of a constituent already present in the sample, the most appropriate constituent is one that is present in all samples of the type to be analyzed, and is present in a readily detectable amount. The constituent will most likely be one that is not of concern, i.e., one whose quantity relative to the other constituents is not indicative of an abnormal condition or is not being monitored, and preferably one whose quantity is nonvariable or nearly so. As in the case of the added marker, the marker already present is preferably one that forms a sharp peak so that a zero point is readily identifiable, and one whose peak is the first peak on the electropherogram, distinct from and non-overlapping with any of the other peaks, i.e., one with the largest electrophoretic mobility. Resolution can be improved further by diluting the sample in a diluent of lower conductivity than the run buffer. Water is one example of such a diluent. When a plug of water passes through the detector window, it produces an artifact that is suitable for determining the electroosmotic mobility.

In preferred methods according to this invention, a single marker is used for both normalization and zero correction, without the use of either a neutral marker, multiple markers, or artifacts of the electropherogram. The information needed is the combination of a good estimate of the electrophoretic mobility of the normalizing marker and its measured migration time. Good estimates can be determined in various ways:

(i) Determining the value each time a sample is run;

(ii) Determining the value once and then tightly controlling conditions so that the value does not change; or (iii) Determining the value for a single selected (reference) sample in a set of samples and moderately controlling conditions under which the other samples in the set are run so that the value does not change.

Of these, (iii) is preferred. A sample with unambiguous and stable features is chosen as the reference sample, and its electrophoretic mobility can be determined in any of the following ways:

(i) Using two added markers;

(ii) Using a single added marker and an additional feature contained in the sample;

(iii) Using a single marker and a best correlation fit to a master electropherogram over a selected region of the electropherogram; or (iv) Using a single marker and a linear least-mean-square fit of the normalized mobilities of a set of the features of that sample to a corresponding set of master features.

Method (iv), which is the "feature fit" referred to above, is the preferred method. In one implementation of this method, the normalized mobilities for a set of features is determined from the measured migration times for the sample by estimating the electrophoretic mobility of the marker, then using these normalized mobilities together with a corresponding master, as defined above, to refine the estimate.

In further preferred embodiments of the invention, zero corrections and normalizations of the vertical axis (for example, absorbance) of the electropherogram are performed as well. Zero correction is achieved by selecting a linear baseline defined by two points where the absorbance of the sample components is substantially zero, and subtracting the values along this baseline from all absorbances. Preferably, the two points are outside and at opposite ends of the region of interest in the electropherogram, to provide a baseline that is subject to the least error. Normalization of the vertical axis can be achieved by reference to the same normalization marker used for normalization of the horizontal (electrophoretic mobility) axis, by multiplying the zero-corrected values by a factor that renders the area or peak height of the normalization marker the same among different electropherograms.

Detection of the solute zones can be achieved by any method that is known to be applicable to capillary electrophoresis, and that will generate an electropherogram capable of computer manipulation for area and peak height determination, normalization and zero correction. One type of detection is ultraviolet absorbance detection. Direct UV-absorbance detection can be achieved by passing a UV beam through the capillary, transverse to the capillary axis, and continuously monitoring the intensity of the beam emerging after having been interrupted by solute zones migrating across its path. Indirect UV-absorbance can be achieved by using a UV-absorbing electrophoretic buffer containing a UV-absorbing ion. Non-UV-absorbing analyte ions are then revealed by changes in light absorption due to displacement of the UV-absorbing buffer ion. UV absorbance can also be detected by a thermooptical method. According to this method, two intersecting laser beams are focused on the capillary, one to be absorbed by analytes in the capillary causing a temperature rise, and the other to monitor refractive index changes caused by the temperature rise. Fluorescence detectors can also be used, with an arc lamp or a laser as the excitation source. Direct fluorescence detection is achieved with a fluorescent label or tag covalently attached to the analyte molecules, either by pre-column or post-column derivatization. For pre-column derivations and on-line detection, various arrangements for isolating the excitation beam from the emission detection are well documented in the literature. For post-column derivatization, the arrangements for reagent introduction and emission detection are likewise documented. Indirect fluorescence detection is achieved in a manner analogous to indirect UV absorbance detection—a fluorescent species is included in the electrophoretic buffer, and analytes are detected by their displacement of the fluorescent species. Other methods of detection that can be used include mass spectrometry detectors, amperometric detectors, conductivity detectors, radiometric detectors, raman-based detectors, and refractive-index detectors. The application of these methods to capillary electrophoresis and their adaptation to particular types of sample mixtures is documented in the literature and well known to those skilled in the art. The preferred method of detection is UV absorbance, and most preferably direct UV absorbance.

As is known, when a window of fixed length is used to detect compounds moving across the window, the amplitudes are multiplied by the velocity at which the compounds traverse the window in order to keep the peak areas proportional to the amount of component. In capillary electrophoresis, this is often achieved by dividing by the migration time. The equivalent correction when the electropherogram is plotted against mobility rather than time is provided by multiplying (rather than dividing) the amplitudes by the migration time.

Normalization, zero correction, and all other data processing and manipulations in the practice of this invention are readily susceptible to software algorithms, including those that are commercially available and those that are capable of readily being developed and adapted by those skilled in the use of software for chromatographic and electrophoretic data. In addition, electrophoretic separations performed in accordance with this invention are well suited to automation, and a variety of automated systems commercially available can be used. One example of a suitable automated system is the Bio-Focus 2000 CE System of Bio-Rad Laboratories, Hercules, Calif., USA. An example of suitable software is the CDM 2.0 software, also available from Bio-Rad Laboratories.

The methods of this invention are of greatest interest for the analysis of biological samples, or the detection and/or quantification of specific components in biological samples. Typical samples include whole blood, plasma, serum, urine and cerebrospinal fluid. Human serum is one of the most common samples in need of analysis.

The following examples are offered for purposes of illustration only.

EXAMPLE 1

A sample of human serum was analyzed by capillary zone electrophoresis in a fused silica capillary under the following conditions:

capillary internal diameter: 25 microns total capillary length: 23.6 cm capillary distance to detection window: 18.6 cm running buffer: Bio-Rad Laboratories, Inc., Catalog No. 194-5055 sample size: amount delivered by application of 5 psi for 1 second running voltage: 12 kV detection: on-line, using UV absorbance at 204 nm The sample was run once with no added marker species, and two electropherograms were generated. In both electropherograms, the albumin peak was used as the normalization marker (and therefore assigned a normalized migration (x-axis) value of −1), and a small peak at the beginning of the separation pattern (an artifact of the electropherogram) was used for zero correction (and therefore assigned a migration (x-axis) value of 0). In one electropherogram, migration time normalized to the albumin peak was used as the x-axis, while the other used mobility normalized to the albumin peak.

FIG. 1 shows the two electropherograms superimposed, the migration-time-normalized electropherogram represented by the dashed line, and the mobility-normalized electropherogram represented by the solid line. The peaks, from left to right, are the protein fractions albumin (at −1 on the x-axis), alpha-1, alpha-2, beta, and gamma, followed by the artifact peak at 0 on the x-axis. The difference between the two separation patterns is apparent, with the mobility-normalized electropherogram exhibiting a sharper normalization peak (albumin) and a broader gamma-region peak (centered at approximately −0.2 on the x-axis). The mobility-normalized gamma-region peak is considerably closer in appearance to its counterpart in a planar gel electrophoresis scan.

EXAMPLE 2

Two different samples of human serum were analyzed in successive separations in the same capillary, using the conditions listed in Example 1. Zero correction was achieved by the same artifact used in Example 1, but normalization was achieved by the introduction of an extraneous charged marker molecule, hippuric acid. In addition to providing normalization for the electrophoretic mobility (x-axis), the hippuric acid further served as normalization for the absorbance (y-axis).

Figure 2:
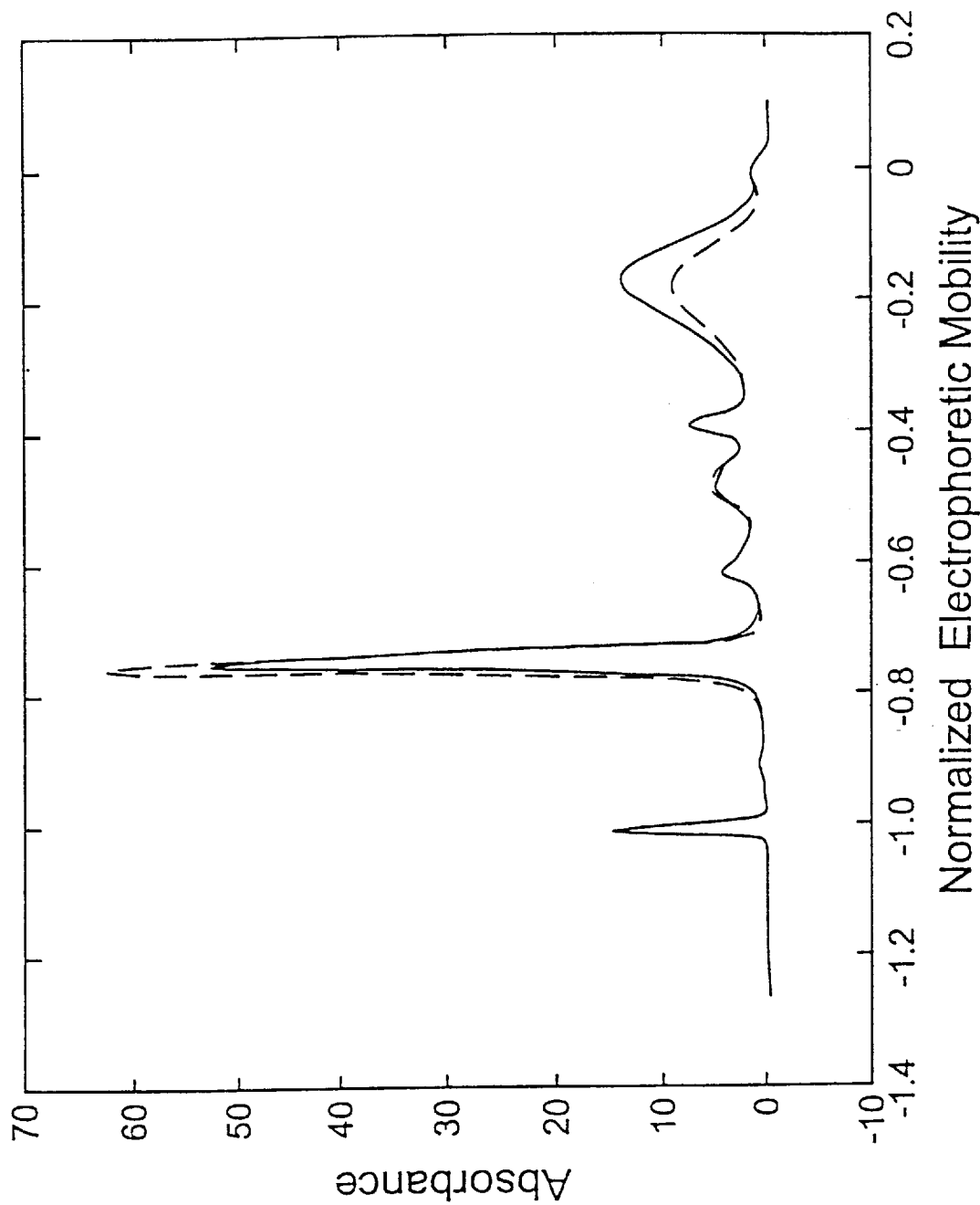
FIG. 2 is a superimposed plot of electropherograms of two different samples, both produced with an added marker in the sample for purposes of mobility normalization, once again using an artifact of the electropherogram for zero correction.

FIG. 2 shows the electropherograms for the two samples superimposed, one sample represented by the solid line and the other by the dashed line. The hippuric acid marker eluted as a peak outside the range of the serum protein peaks, and was assigned a mobility of −1. In addition, the y-axis was zero corrected by subtracting the values of a linear (in migration time) baseline drawn between a point to the left of the hippuric acid peak and a point to the right of the artifact (zero correction peak). The zero-corrected absorbance values were multiplied by the mogration time and then normalized by adjustment such that the hippuric acid peak areas were the same. The two serum samples were selected for differences in the amount of albumin and gamma-region proteins, and this is evident from a comparison of the peak heights and areas. Note that all other peaks are substantially identical between the two electropherograms.

EXAMPLE 3

This example illustrates mobility normalization and zero correction of an electropherogram without the use of either an added zero marker or an artifact of the electropherogram as a zero marker.

Two different samples of human serum were again analyzed in successive separations in the same capillary, using the conditions listed in Example 1, except that detection was performed at 225 nm rather than 204 nm. The zero-peak artifact observable at 204 nm is essentially indistinguishable at 225 nm. Hippuric acid was once again added to serve as a normalization marker, but also in this case for zero correction, based on its migration time and its mobility, using the relationship of Equation (7) above. The electrophoretic mobility of the hippuric acid had been independently determined from the runs of Example 2.

Figure 3:
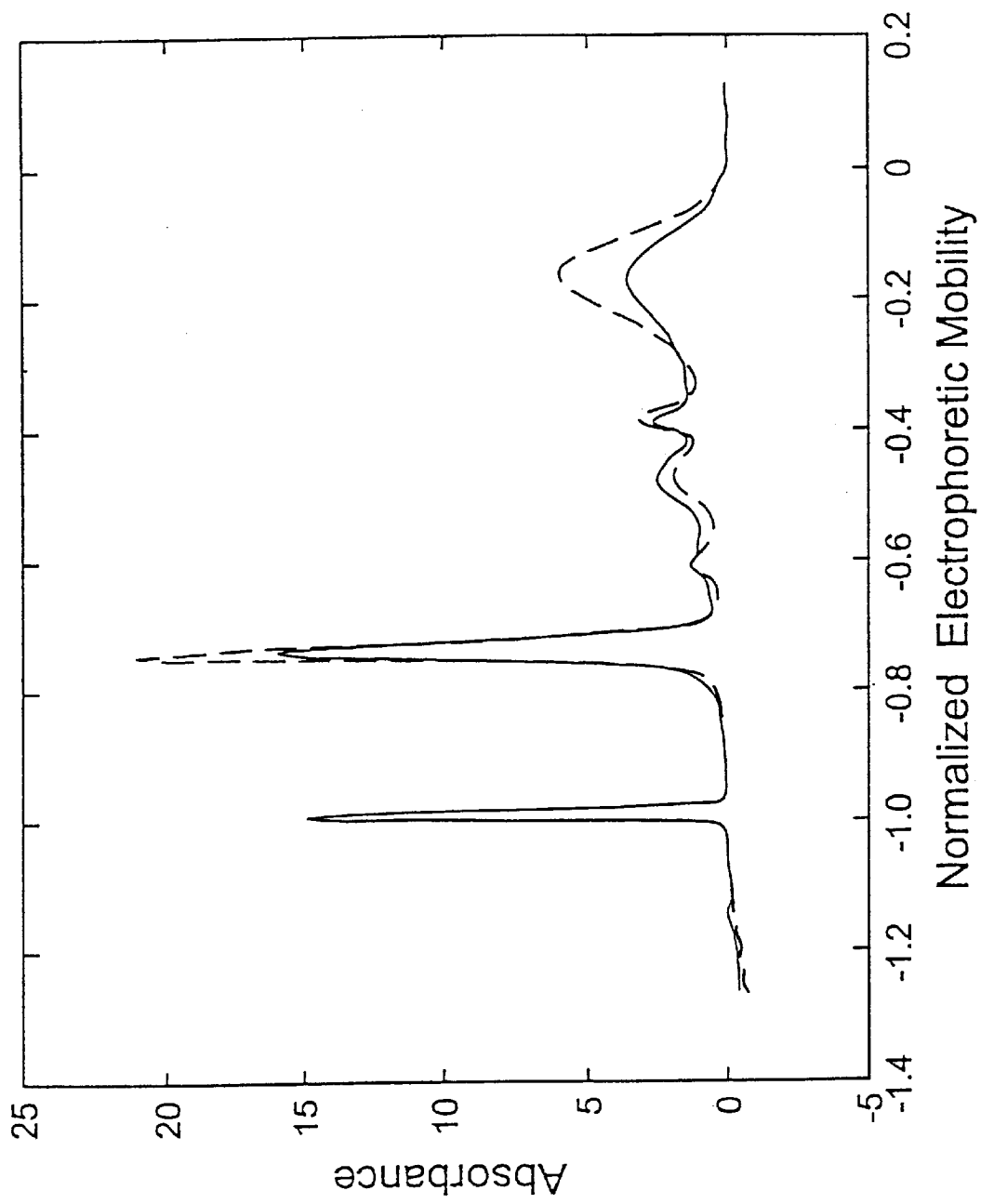
FIG. 3 is a superimposed plot of electropherograms of two additional samples, both produced with an added marker in the sample for purposes of mobility normalization, but using the same marker for zero correction.

The two electropherograms, with x-axis normalized by mobility and zero corrected, and y-axis zero-corrected and normalized by the peak area of the hippuric acid peak, are superimposed in FIG. 3. One sample is represented by the solid line and the other by the dashed line. The two samples differed in the amounts of all fractions except alpha-1, and this is evident from a comparison of the peak heights and areas.

EXAMPLE 4

This example illustrates the use of the "feature fit" method to determine the electrophoretic mobility of the normalizing marker in a reference, such as the reference shown in dashed lines in FIG. 3. No neutral marker or artifact is easily distinguishable in that reference. For purposes of illustrating the method, a neutral marker, mesityl oxide, has been added to the reference. The electropherogram is shown in FIG. 4, where the electropherogram is represented twice in a superimposed plot, one (appearing as a dashed line) using an estimate for the electrophoretic mobility of the marker that was not refined by a feature fit, and the other (appearing as a solid line) using an estimate that was refined by the feature fit.

Figure 5:
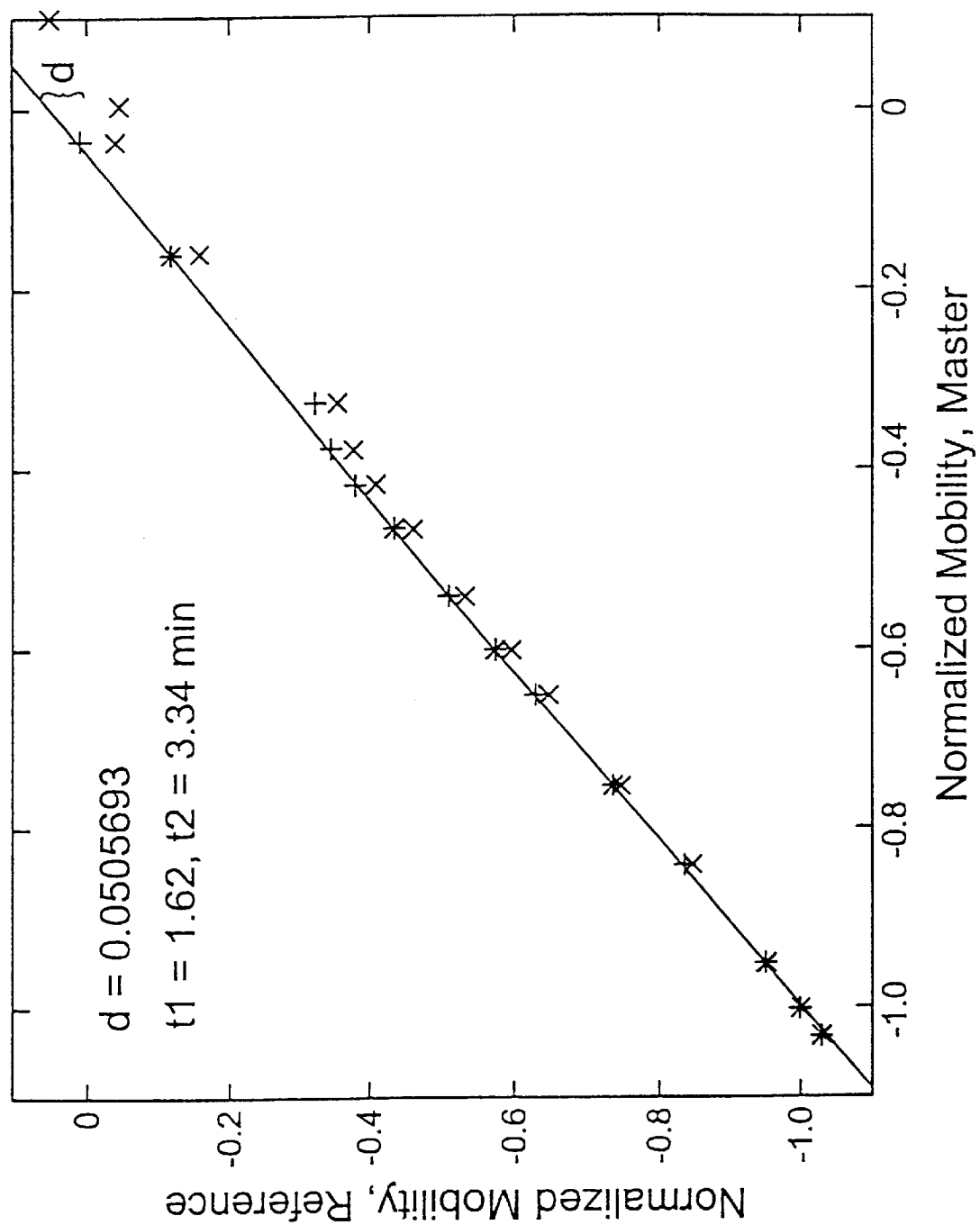
FIG. 5 is a scatter plot of mobilities from FIG. 4, using a least mean square linear fit, which is then used to obtain the refined estimate shown in FIG. 4.

The method of obtaining the feature fit was a least mean square linear fit, which is illustrated in FIG. 5. The locations of the features found in the oiriginal estimate are plotted using plus (+) symbols as y-values against the expected location of the features, which are plotted as x-values. For the features that have been selected for the feature fit, i.e., assigned a weight of 1, asterisks are superimposed over the plus symbols. All other features have been assigned a weight of zero and thereby not used in the fit. The straight line fit has been forced through the coordinates (−1, −1), and intercepts the x=0 axis at y=d, which is 0.05057 for this example.

Figure 4:
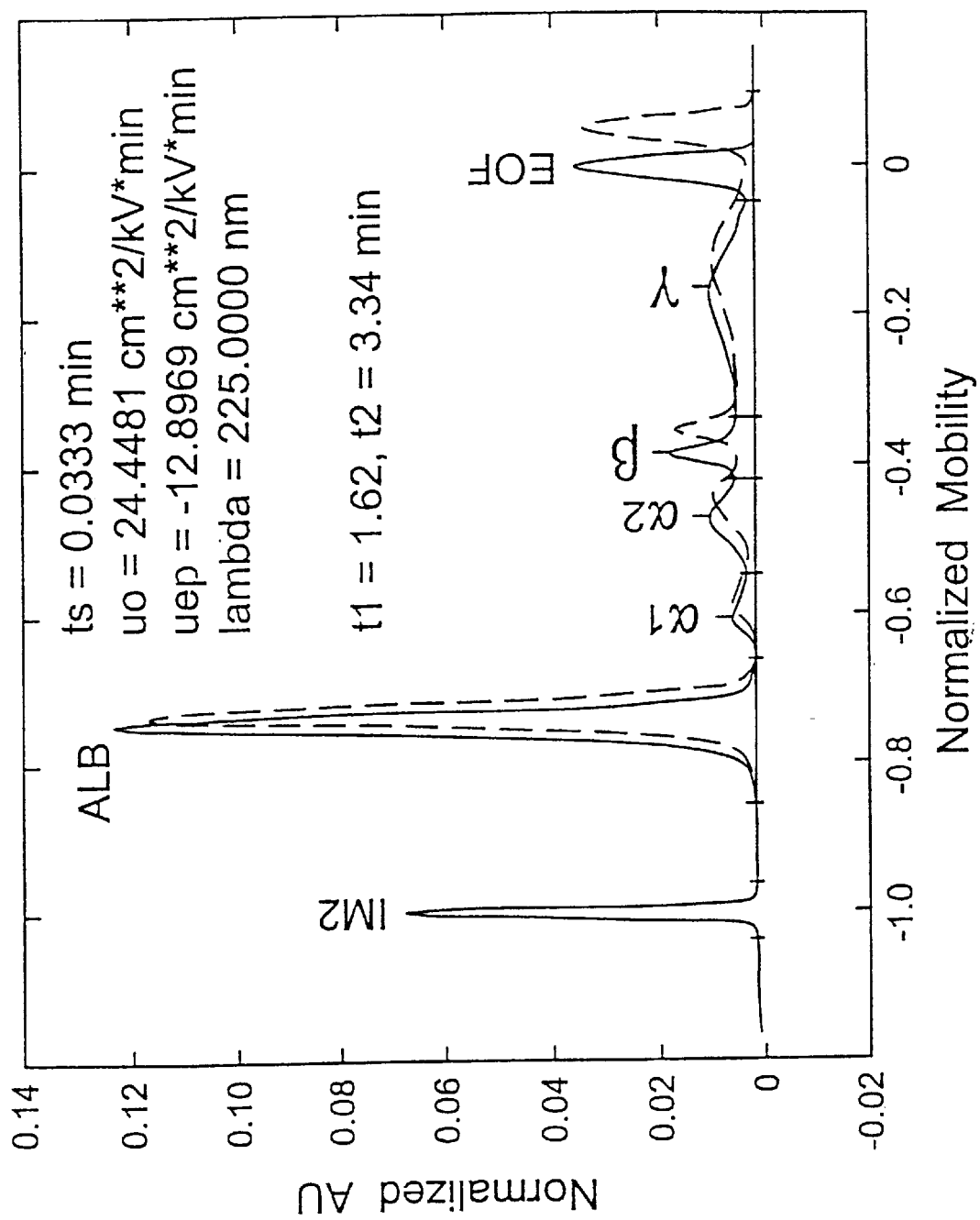
FIG. 4 is a superimposed plot of two electropherograms of the same sample, one plotted using an estimate of the electrophoretic mobility of the marker and the other plotted after refining this estimate by feature fit.

The value of d thus determined is used in Equation (11) above to correct all other mobilities in FIG. 4, where the corrected electropherogram appears as the solid line. The corrected y-values of the features were then plotted in FIG. 5 using X symbols. The corrected value of the electrophoretic mobility of the marker for this reference is determined using Equation (9) above. This value serves as a good estimate for the reference used for patient samples run in the same sample set. This value is used in Equation (7) to calculate the electroosmotic mobility and in Equations (5) and (8) to calculate all other mobilities, for patient samples associated with that reference.

The foregoing is offered primarily for purposes of illustration. It will be readily apparent to those skilled in the art that the operating conditions, materials, procedural steps and other parameters of the systems and methods described herein may be further modified or substituted in various ways without departing from the spirit and scope of the invention.

What is claimed is:

1. A method of detecting a constituent species in a sample by capillary electrophoresis, said method comprising:
   (a) subjecting said sample to capillary electrophoresis in a buffer solution to cause continuous flow of said sample or components thereof past a fixed locus in the path of said electrophoresis, and continuously detecting a value representative of the composition of said buffer solution at said fixed locus;
   (b) generating an electropherogram of (i) said value thus detected as a function of (ii) the ratio of zero-corrected total mobility to the zero-corrected total mobility of a selected marker in said sample; and
   (c) comparing said electropherogram to an electropherogram of a known composition containing said constituent species to identify said constituent species if present in said sample.

2. A method in accordance with claim 1 in which (c) further comprises determining the amount of said constituent species in said sample.

3. A method in accordance with claim 1 in which said constituent species is defined as a first constituent species, and selected marker is a second constituent species of said sample, said second constituent species is a charged species known to be present in said sample and having an electrophoretic mobility differing from that of said first constituent species.

4. A method in accordance with claim 1 in which said selected marker is a charged species added to said sample and not otherwise present therein.

5. A method in accordance with claim 4 in which said charged species has a mobility with an absolute value exceeding the mobilities of all suspected constituent species of said sample.

6. A method in accordance with claim 4 in which said charged species has molecular weight of less than about 250.

7. A method in accordance with claim 4 in which said charged species has molecular weight of less than about 250 and a charge density of at least about 0.001.

8. A method in accordance with claim 4 in which said charged species has molecular weight of from about 100 to about 250.

9. A method in accordance with claim 4 in which said charged species has molecular weight of from about 100 to about 250, and a charge density of from about 0.001 to about 0.03.

10. A method in accordance with claim 1 in which (b) comprises zero correcting said total mobility by correcting said total mobility relative to a selected peak in said electropherogram.

11. A method in accordance with claim 1 in which (b) comprises zero correcting said total mobility by correcting said total mobility relative to an identifiably distinct point in said electropherogram.

12. A method in accordance with claim 1 in which (b) comprises zero correcting said total mobility by adding a neutral species to said sample that is not otherwise present therein and correcting said total mobility relative to a peak in said electropherogram corresponding to said neutral species so added.

13. A method in accordance with claim 1 in which said selected marker used in (b) is a charged species, and in which (b) comprises zero correcting said total mobility by adding a neutral species to said sample that is not otherwise present therein and correcting said total mobility relative to a peak in said electropherogram corresponding to said neutral species so added, said neutral species and said charged species having different mobilities.

14. A method in accordance with claim 1 in which said selected marker has a known electrophoretic mobility and a known migration time, and (b) comprises zero correcting said total mobility relative to a calculated electroosmotic mobility derived solely from said known electrophoretic mobility and said known migration time.

15. A method in accordance with claim 1 in which said sample is one sample among a plurality of samples in a sample set, each containing a selected marker; said selected markers are charged markers; and said method further comprises including a reference sample in said sample set and determining from said sample the electrophoretic mobility of the charged markers in all other samples in said sample set.

16. A method in accordance with claim 15 in which said reference sample contains both a charged and a neutral marker and both are used to determine the electrophoretic mobility of said charged markers.

17. A method in accordance with claim 15 in which said reference sample contains only a single charged marker that is used together with other known features of said reference sample to determine the electrophoretic mobility of said charged markers.

18. A method in accordance with claim 1 in which said selected marker is a charged species added to said sample and not otherwise present therein, said charged species having a known electrophoretic mobility and a measured migration time with absolute values exceeding the electrophoretic mobilities and migration times, respectively, of all suspected constituent species of said sample, and (b) comprises zero correcting said total mobility relative to a calculated electroosmotic mobility derived solely from said known electrophoretic mobility and said measured migration time.

19. A method in accordance with claim 1 in which said value continuously detected in (a) is absorbance.

20. A method in accordance with claim 1 in which said value continuously detected in (a) is fluorescence.

21. A method in accordance with claim 1 in which said selected marker is a species added to said sample and not otherwise present therein.

22. A method in accordance with claim 21 in which said added species is a charged species having a mobility with an absolute value exceeding the mobilities of all suspected constituent species of said sample.

23. A method in accordance with claim 1 in which said sample is a sample of biological fluid.

24. A method in accordance with claim 1 in which said sample is a member selected from the group consisting of whole blood, plasma, serum, urine and cerebrospinal fluid.

25. A method in accordance with claim 1 in which said sample is human serum.

26. A method in accordance with claim 1 in which (a) comprises continuously detecting absorbance at a wavelength within the range of about 180 nm to about 300 nm.

27. A method in accordance with claim 1 in which (a) comprises continuously detecting absorbance at a wavelength within the range of about 200 nm to about 250 nm.

28. A method in accordance with claim 1 in which (b) and (c) are performed by automated instrumentation governed by computer software.

29. A method in accordance with claim 1 in which (a), (b) and (c) are performed by automated instrumentation governed by computer software.

30. A method in accordance with claim 1 in which said capillary has an inner wall of molecular species containing negatively charged groups, and said constituent species is negatively charged.

31. A method in accordance with claim 1 in which (c) comprises visually comparing said electropherograms.

32. A method in accordance with claim 1 in which (c) comprises comparing said electropherograms quantitatively.

33. A method in accordance with claim 1 in which said value continuously detected in (a) is absorbance, in which (c) further comprises deriving the amount of said constituent species in said sample from the amplitude of a peak of said electropherogram associated with said constituent species.

* * * * *